United States Patent [19]

Frazer

[11] Patent Number: Plant 6,855

[45] Date of Patent: Jun. 13, 1989

[54] DIEFFENBACHIA HYBRIDA TAHITI

[75] Inventor: Edwin J. Frazer, Brisbane, Australia

[73] Assignee: Hartman Plant Laboratories, Inc., Santa Paula, Calif.

[21] Appl. No.: 23,604

[22] Filed: Mar. 9, 1987

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Hale and Dorr

[57] ABSTRACT

A new and distinct cultivar of Dieffenbachia known as Dieffenbachia Hybrida Tahiti, which is a seedling cross between Marianne and Wilson's Delight.

1 Drawing Sheet

The invention comprises a new and distinct cultivar of Dieffenbachia known as Dieffenbachia hybrida Tahiti.

The new cultivar is a product of a seedling cross between Dieffenbachia Marianne and Wilson's Delight.

The following observations, measurements and values describe plants grown in Alva, Fla. under greenhouse conditions that closely approximate those generally used in horticultural practice. All color references are measured against the Royal Horticultural Society Colour Chart. Colors are approximate as color depends on horticultural practices such as light level and fertilization rate among others.

The following traits have been repeatedly observed to be characteristics which in combination distinguish Diffenbachia Tahiti from other commercially available Dieffenbachia.

Distinctions

1. Larger, broader leaves than Compacta.
2. The same color pattern as Compacta but the pattern is more irregular.
3. Midribs are white on both sides of the leaves.
4. More breaks than Perfection but less than Compacta.
5. The petioles clasp the stem but diverge from the stem as the leaf ages.
6. The petiole and wings are broad.
7. The midribs are flexible enough to bend double without breaking.
8. The new leaves are yellowish fading to white as the leaf ages.
9. Taller than Compacta.

The appearance and distinctive character of Tahiti is shown in the FIGURE which is a true color photograph of the cultivar in an eight-inch pot.

DESCRIPTION

Propagation: Asexual production either through tissue culture or division.

Plant: In a 6 inch pot, Tahiti will be approximately 24 cm to 28 cm from the soil surface to the in junction of the petioles of the last two unrolled leaves and approximately 41 cm to 47 cm in width after approximately 26 to 36 weeks under appropriate growing conditions from tissue culture. All measurements are based on the above parameters.

Stem:

*Growth pattern.*—The stem is erect in growth and will be approximately 2.0 cm to 2.3 cm in diameter 5 cm above the soils surface. Internode distance will be approximately 1.5 cm to 1.9 cm at a height of 3 cm above the soil.

*Color.*—The stem is green with very faint light green stripes.

Petiole (Based on the fourth expanded leaf from apex of the main shoot):

*Pattern.*—The petiole has fleshy edges extending from the midrib that will be referred to as wings. The wings will be approximately 9 mm to 11 mm wide 1 cm below the leaf base. The wings extend from the base of the petiole to the leaf base on mature sized leaves only. The apex of the wings is emarginate. The petiole follows the stem axis but diverges from the axis approximately 0.7 cm to 1.0 cm from the leaf base forming a horizontal distance from the edge of the stem to the leaf base of approximately 0.7 cm to 1.0 cm.

*Physical dimensions.*—The petiole will be approximately 7.0 cm to 7.6 cm from its base to the base of the leaf. The petiole will be approximately 6 mm to 8 mm in diameter one half way between the top of the wing to the bottom of the leaf.

*Color and color pattern.*—The petiole wings will be green and the midrib will be cream white.

Leaf:

Growth pattern.—The leaf will be ovate with a acuminate/aristate apex and a cordate base. The margin is entire. The leaf is asymmetric with the side of the leaf unrolling first having less surface area and less undulations on the leaf margin than the side unrolling last. The leaf is oriented 45° to the stem axis at the time of full unrolling changing to 80° to the stem axis as more leaves unroll above it. The midrib droops slightly over the length of the leaf. The leaf blade is flat from the midrib to the margin.

*Physical dimensions.*—For the potsize and growing time indicated, the largest leaf will be approximately 22 cm to 26 cm long and approximately 12 cm to 14 cm wide. An average sized leaf will be approximately 19 cm to 22 cm long and approximately 10 cm to 12 cm wide. The leaf thickness is medium.

*Midrib.*—The midrib is thick and white with a little green at the base.

*Primary veins.*—The primary veins are sunken into the adaxial side and protruding out of the abaxial side.

*Color and pattern.*—The adaxial surface of the mature, older leaf has a midrib color of 155C, and a leaf blade background color of 139A, blotched with irregular areas of 155C, 157C radiating from the midrib.

The abaxial surface of the mature, older leaf has a midrib color of 156D, with veins of 156D, changing to the leaf blade background color near the leaf edge; the leaf blade background color is 137B, 191A, with blotches of 138B.

The adaxial surface of the newly-opened leaf has a midrib color of 157C and a leaf blade color greener than 139A with blotches of 1C radiating from the midrib. The abaxial surface of the newly-opened leaf has a midrib color of 145B at the base of the leaf, changing to 150D on approach to the apex, and a leaf blade background color of 138A, blotched with 149D.

*Texture.*—The leaf surface is rigged and has a dull appearance.

Axillary breaks: There will be approximately 12 to 18 axillary breaks with at least 1 leaf expanded. Leaves will show color by the first leaf and will have true color and pattern by the third leaf.

Inflorescences: Not present.

Roots: Thick white roots with finer laterals.

General observations: Dieffenbachia Tahiti is a compacta or perfection type but differs in the following ways. Tahiti is slightly taller than Compacta and has larger leaves. The leaf pattern is not as regular as Compacta. The midrib is white on both sides of the leaf. Tahiti does not break as well as Compacta, however the larger leaves give the plant an appearance of being just as dense. The petioles are more colorful than compacta. Tahiti's new leaves are yellower than the new leaves of Compacta.

The midribs are flexible enough to permit bending the leaves without damage.

I claim:

1. A new and distinct cultivar of Dieffenbachia as described and illustrated.

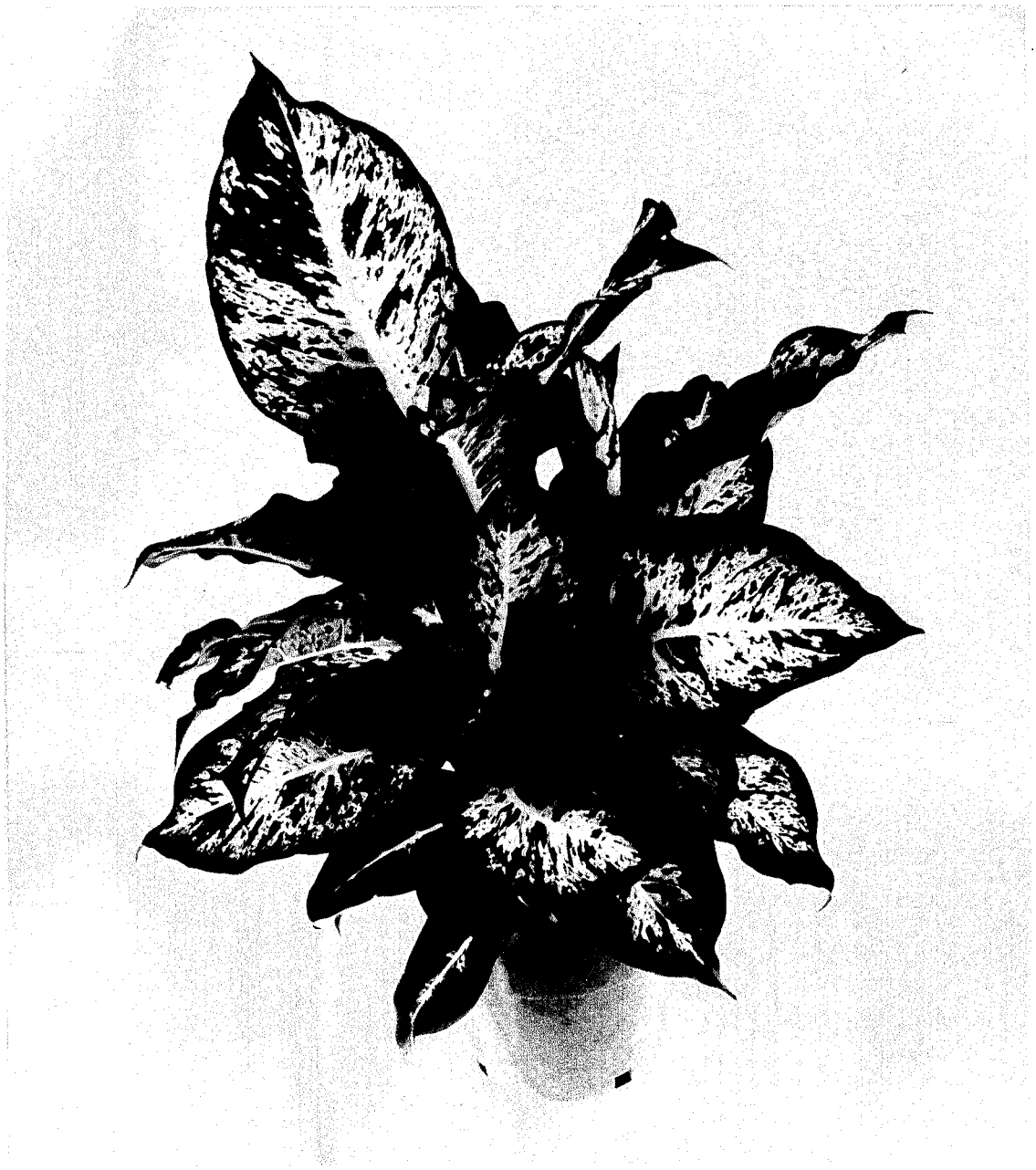

* * * * *